United States Patent [19]

Cantello et al.

[11] 4,014,907

[45] Mar. 29, 1977

[54] 2-HYDROXY-3-NITRO-1,4-NAPHTHOQUINONES

[75] Inventors: Barry Christian Charles Cantello; Derek Richard Buckle, both of Redhill; Harry Smith, Maplehurst near Horsham, all of England

[73] Assignee: Beecham Group Limited, England

[22] Filed: Apr. 24, 1975

[21] Appl. No.: 571,253

[30] Foreign Application Priority Data

May 28, 1974 United Kingdom ............ 23563/74

[52] U.S. Cl. ............................. 260/396 R; 424/331
[51] Int. Cl.² ................... C07C 49/62; C07C 49/66
[58] Field of Search ............ 424/331; 260/590 FA, 260/590 FB, 396 R

[56] References Cited

UNITED STATES PATENTS

| | | | |
|---|---|---|---|
| 3,833,726 | 9/1974 | Schwender et al. | 424/331 X |
| 3,920,845 | 11/1975 | Smith et al. | 424/331 |

OTHER PUBLICATIONS

Vladimirtsev et al., Chemical Abstracts 73:1190f, (1970).
Ikeda et al., Chemical Abstracts 50:3358d, (1956).

*Primary Examiner*—Norman A. Drezin

[57] ABSTRACT

Substituted naphthoquinones of the formula (I) and pharmaceutically acceptable salts thereof wherein $R_1$, $R_2$, $R_3$ and $R_4$ represent alkyl, aryl, alkoxy, hydroxy, hydrogen or halogen or any two of the groups $R_1$, $R_2$, $R_3$ and $R_4$ taken together complete a carbocyclic ring, have useful anti-allergy activity in mammals.

11 Claims, No Drawings

2-HYDROXY-3-NITRO-1,4-NAPHTHOQUINONES

This invention relates to pharmaceutical compositions which are useful in the inhibition of the effects of certain types of antigen-antibody reactions, and are therefore of the value in the prophylaxis and treatment of diseases associated with allergic or immunological reaction e.g. certain types of asthma and hay-fever and also in the treatment of rhinitis. The invention also includes a number of new substituted nitro-tri-keto tetralins and a method for their preparation, as well as intermediates useful in their preparation.

2-Hydroxy-3-nitro-1,4-naphthoquinones of formula (I):

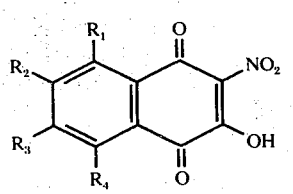

and pharmaceutically acceptable salts thereof, wherein the groups $R_1$, $R_2$, $R_3$ and $R_4$ are each a hydrogen or halogen atom, or an alkyl, aryl, alkoxy or hydroxy and any two of the groups $R_1$, $R_2$, $R_3$ and $R_4$ taken together may complete a carbocyclic ring, have useful activity in mammals in that they inhibit the effects of certain types of antigen-antibody reactions.

A literature search has revealed that one of the compounds of the formula (I) is not novel. More specifically, the compound 2-hydroxy-3-nitro-1,4-naphthoquinone has been reported by K. Miyaka and N. Ikeda, J. Pharm Soc. Japan, 74, 655, 1954. However no form of useful biological activity has been ascribed to the compound. Likewise there has been in the literature, no suggestion that such a compound is likely to possess any form of useful biological activity and in particular the discovery that it has anti-allergic activity has been predicted in any way.

Accordingly, in its broadest aspect, the present invention provides a pharmaceutical composition having anti-allergy activity comprising a compound of formula (I) or a pharmaceutically acceptable salt thereof:

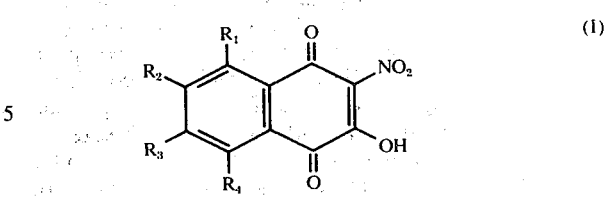

together with one or more pharmaceutically acceptable carriers, wherein the groups $R_1$, $R_2$, $R_3$ and $R_4$ represent hydrogen, alkyl, alkoxy, aryl, hydroxy or halogen and any two of the groups $R_1$, $R_2$, $R_3$ and $R_4$ taken together complete a carbocyclic ring being adapted for administration to human beings.

Examples of the groups $R_1$, $R_2$, $R_3$ and $R_4$ which may be present in compounds of the formula (I) include hydrogen, fluorine, chlorine, bromine and iodine atoms, and methyl, ethyl, n- and iso- propyl, n-, sec- and tert-butoxy, phenyl. In addition the groups $R_1$ and $R_2$, $R_2$ and $R_3$ or $R_3$ and $R_4$ taken together may complete benzene, cyclohexenyl or cyclopentenyl ring.

Preferably the groups $R_1$ and $R_4$ are each hydrogen atoms, and the groups $R_2$ and $R_3$ are each methyl, ethyl, n-propyl, methoxy, ethoxy or n-propoxy groups, or $R_2$ and $R_3$ taken together complete cyclohexenyl or cyclopentenyl ring.

Examples of suitable salts of compounds of the formula (I) include the alkali metal salts, particularly potassium and sodium, and the alkaline earth metal salts, magnesium salts or aluminium salts, as well as salts with organic bases such as amines or amino compounds.

The compounds of formula (I) may exist in a number of tautomeric forms, and it is to be understood that whenever in the specification we refer to compounds of the formula (I) we mean to include tautomeric forms thereof.

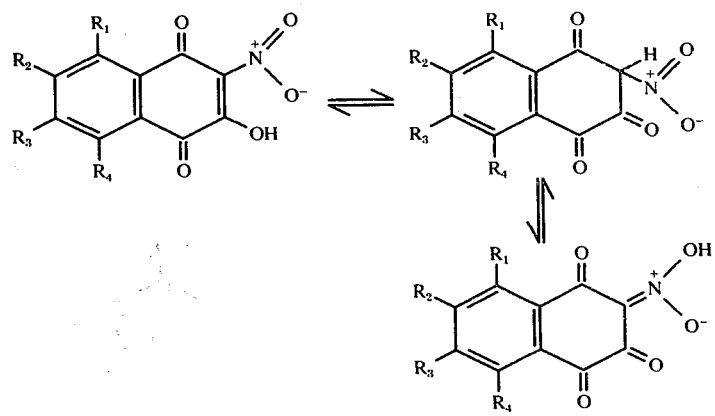

ture, no suggestion that such a compound is likely to possess any form of useful biological activity and in particular the discovery that it has anti-allergic activity has been predicted in any way.

The compositions of this invention may be presented as a microfine powder for insufflation, e.g. as a snuff or in capsules of hard gelatin. They may also be presented with a sterile liquid carrier for injection. Compounds of formula (I) which are active when given by the oral route, may be compounded in the forms of syrups, tablets, capsules, pills and the like. Preferably the compositions are in unit dosage form, or in a form which the patient can administer to himself in a single dosage. For example when the composition is in the form of a tablet, pill or capsule, a suitable dosage unit might contain from 1 to 50 mg of active ingredient. If desired, a small amount of bronchodilator compound such as isoprenaline may be incorporated into the compositions of this invention both to inhibit the cough response if the composition is insufflated and to provide immediate relief during an asthmatic attack. The effective dose of compound (I) depends on the particular compound employed, but is in general in the range of from 0.1 mg/kg/day to 100 mg/kg/day.

The precise nature of the pharmaceutical carrier used in the compositions of this invention is not important. Standard pharmaceutical practice may be followed.

As is common practice, the compositions will usually be accompanied by written or printed directions for use in the medical treatment concerned, in this case as an anti-allergic agent for prophylaxis treatment of, for example, asthma, hay-fever or rhinitis.

In a second aspect, the invention provides novel compounds of the formula (I):

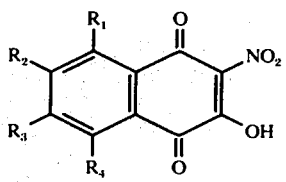

(I)

and pharmaceutically acceptable salts thereof, wherein the groups $R_1$, $R_2$, $R_3$ and $R_4$ are each a hydrogen or halogen atom, or an alkyl, aryl, aralkyl, alkoxy, aryloxy, aralkoxy, heterocyclic, or hydroxy, and any two of the groups $R_1$, $R_2$, $R_3$ and $R_4$ taken together may complete a carbocyclic ring; except the compound 2-hydroxy-3-nitro-1,4-naphthoquinone and pharmaceutically acceptable salts thereof.

The identities and the preferred values of the groups $R_1$, $R_2$, $R_3$ and $R_4$ have already been discussed in relation to the pharmaceutical compositions of the invention, and the same remarks apply here in relation to these novel compounds.

The invention further provides a process for the preparation of these novel compounds, which process comprises nitrating the parent compound of the formula (II):

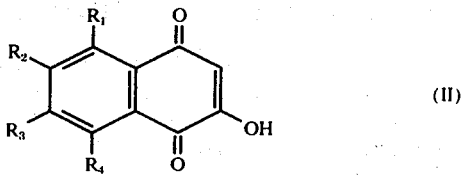

(II)

wherein the groups $R_1$, $R_2$, $R_3$ and $R_4$ are as defined with reference to formula (I), except that compound in which the groups $R_1$, $R_2$, $R_3$ and $R_4$ are not all hydrogen atoms, and thereafter if desired converting the thus formed compound of the formula (I) to a pharmaceutically acceptable salt thereof.

As nitrating agent we prefer to use fuming nitric acid, and the reaction is suitably carried out in an inert solvent at an ambient or slightly lowered temperature. While the choice of solvent and temperature is not critical to the success of the reaction, we have found that the reaction procedes smoothly in chloroform at room temperature.

Other conventional nitrating agents may be used to effect the required conversion. These include:
  i. The nitrous fumes generated with concentrated nitric acid and arsenic oxide.
  ii. Acetic acid together with concentrated nitric acid.
  iii. Concentrated nitric acid.

The 2-hydroxy-1,4-naphthoquine precursors used in the preparation of the novel compounds of this invention may be prepared by two routes. The method of choice will depend upon the nature of the substitution required, and the availability of starting materials.

Route 1 involves the Diels-Alder addition of a suitable 1,3-diene (III) to p-benzoquinone. The resultant Diels-Alder addduct (IV) is isomerised and oxidised to a 1,4-naphthoquinone (V):

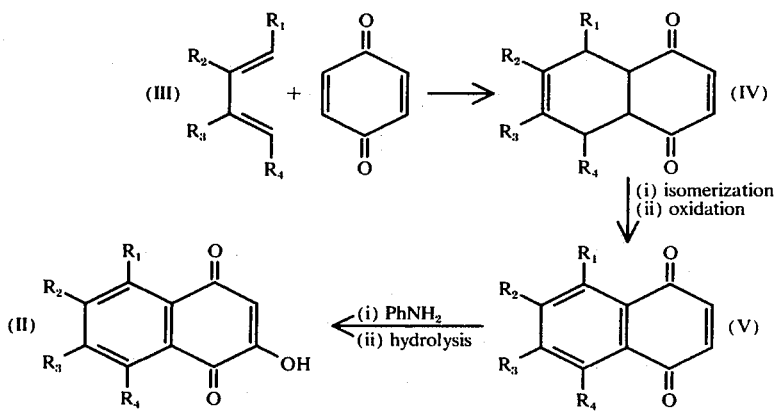

The 1,4-naphthoquinone is reacted with aniline, according to the method of Lyons & Thomas, J. Chem. Soc. 1953 Page 910, and the product then hydrolyzed with, for example, dilute sulphuric acid, to yield the corresponding compound of the formula (II). (When the groups $R_1$, $R_2$, $R_3$ and $R_4$ are such that the compound of the formula (V) is asymmetrically substituted in the phenyl ring, the position of hydroxyl substitution to be expected in the quinone ring is discussed by Lyons and Thomson, loc. cit., and Macleod and Thomson, J. Org. Chem. 25, 36, (1960)).

Route 2 involves the Friedel-Craft acylation of a substituted benzene (VI) with succinic anhydride, to yield a keto acid (VII). This keto acid is reduced and cyclized with polyphosphoric acid to yield the tetralone (VIII). Tetralones of formula (VIII) can be readily converted to 2-hydroxy-1,4-naphthoquinones of formula (IX) by autoxidation using the procedures disclosed by Baillie and Thomson in J. Chem. Soc. (C) 1966, page 2184 and by Kasturi and Arunachalam in Canad. J. Chem. 1966 vol. 44 page 1086.

hydrochloric acid gave material of m.p. 161°–2° C (d). (Lit m.p. 160°–161° C A. Inoue, N. Kuroki and K. Konishi CA 54 4504 g (1960). (Found; C, 54,99; H, 2.59; N, 6.30; $C_{10}H_5NO_5$ requires; C, 54.80; H, 2.30; N, 6.39%).

A suspension of 2,3-dichloro-1,4-naphthoquinone (6.83g; 0.03 mole) in methanol (40 ml) was stirred during the addition of a solution of sodium nitrite (6.9g; 0.1 mole) in water (50ml) and the mixture stirred at 80° C for 3 hours. Solution was attained after

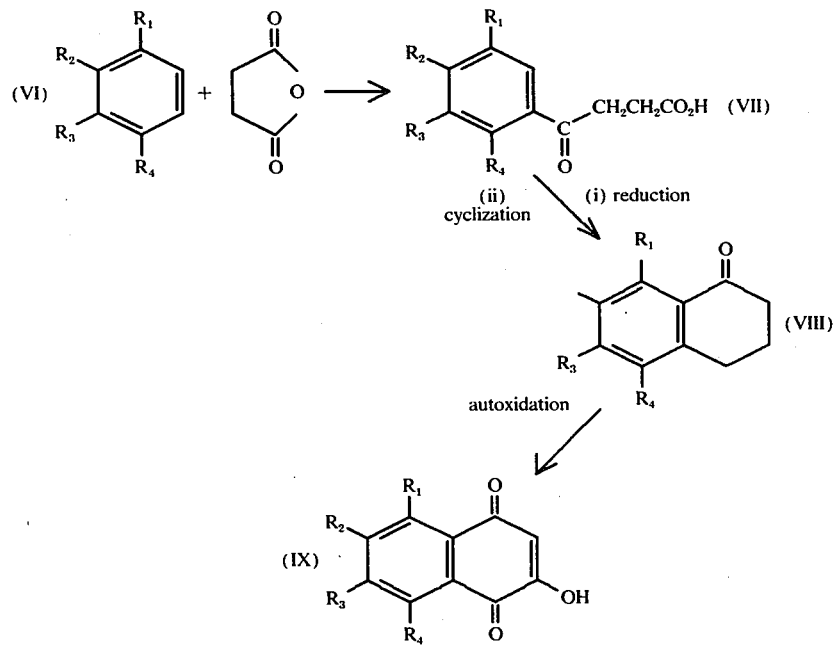

The novel compounds of formula (I) can also be prepared from the intermediates of formula (X):

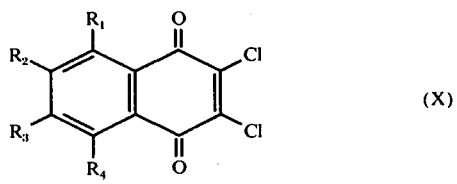

wherein $R_1$, $R_2$, $R_3$ and $R_4$ are defined as in formula (I), which process comprises reacting the intermediates with sodium nitrite in aqueous alkanol. (Miyaka & Ikeda Loc. Cit).

The novel intermediates of formula (X) are prepared from substituted 1,4-naphthoquinone of formula (V) by direct chlorination using standard procedures.

EXAMPLE 1

2-Hydroxy-3-nitro-1,4-naphthoquinone a. Fuming nitric acid (10ml; d 1.52) was added to a stirred suspension of 2-hydroxy-1,4naphthoquinone (2.0g) in chloroform (200ml) at room temperature over 1 hr. After a further 1 hr. the solvent was removed in vacuo without heating and 5N hydrochloric acid (50ml) was added to the residue. Filtration gave 1.84g (73%) of yellow product of m.p. 152°–153° C (d). Recrystallization from water;

about 1 hr and the nitro naphthoquinone began to separate after 2 hrs. After cooling in ice and the yellow crystalline solid was filtered off, taken up in water (200ml), charcoalized and precipitated the product by addition of one-third the volume of concentrated hydrochloric acid, filtered off, washed well with 5N HCl and dried in vacuo over $P_2O_5$/NaOH to give 5.30 g (81%) of material of m.p. 162°–163° C (d) which was identical to that prepared above.

EXAMPLE 2

2-Hydroxy-6-methyl-3-nitro-1,4-naphthoquinone

Fuming nitric acid (5ml, d 1.52 ) was added to a stirred suspension of 2-hydroxy-6-methyl-1,4-naphthoquinone (1.0g) in chloroform (100ml) over 1 hr. at room temperature and after a further 1 hr. the yellow product, 0.90g (73%) was isolated as in example 1(a). Recrystallization from water; hydrochloric acid gave m.p. 159°–160° C (d). (Found; C, 56.57; H, 3.04; N, 5.88; $C_{11}H_7NO_5$ requires; C, 56.66; H, 3.03; N, 6.01%).

EXAMPLE 3

3,5-Dihydroxy-2-nitro-1,4napthoquinone

Nitration of 3,5-dihydroxy-1,4naphthoquinone (1.04g) as described in example 1 (a) afforded 0.654g (51%) of the 2-nitro derivative as orange needles. Recrystallization from water; hydrochloric acid gave m.p. 168°–169° C (d). (Found; C, 50.31; H, 2,09; N, 6.04; $C_{10}H_5NO_6$ requires; C, 51.08; H, 2.14; N, 5.96%).

EXAMPLE 4

3Hydroxy-5-methyl-2-nitro-1,4-naphthoquinone

A solution of 3-hydroxy-5methyl-1,4-naphthoquinone (1.9g) in chloroform (200ml) was nitrated with fuming nitric acid according to example 1(a). A yield of 1.01g (43%) of material of m.p. 148°–149° C (d) was obtained. (Found; C, 56.69; H, 3.16; N, 5.73; $C_{11}H_7NO_5$ requires; C, 56.66; H, 3.03; N, 6.01%).

EXAMPLE 5

3-Hydroxy-6-methoxy-2-nitro-1,4-naphthoquinone

Nitration of a stirred solution of 3-hydroxy-6-methoxy-1,4-naphthoquinone (2g) as described in example 1(a) gave 2.29 (94%) of the nitro derivative of m.p. 152°–155° C. Recrystallization from water; hydrochloric acid raised the m.p. to 159° C. (Found; C, 53.11; H, 3.03; N, 5.78; $C_{11}H_7NO_6$ requires; C, 53.01; H, 2.83; N, 5.62%).

EXAMPLE 6

3-Hydroxy-6-methyl-2-nitro-1,4-naphthoquinone

Nitration of 3-hydroxy-6-methyl-1,4-naphthoquinone (2.0g) as described in example 1(a) gave 2.41g (97%) of the yellow 2-nitro derivative of m.p. 160° C. (Found; C, 56.73; H, 3.00; N, 5.75; $C_{11}H_7NO_5$ requires; C, 56.66; H, 3.03; N, 6.01%).

EXAMPLE 7 a. 2-Anilino-6,7-dimethyl-1,4-naphthoquinone

To a warm solution of 6,7-dimethyl-1,4-naphthoquinone (1.08g; 0.058 mole) in ethanol (20ml) was added aniline (0.5ml) and the red solution refluxed for 1 hr. on a steam bath. After standing overnight the red crystalline anilino derivative was filtered off and recrystallized from acetic acid; water to give 0.54g (34%) of material of m.p. 208°–210° C. (Found; C, 78.02; H, 5.47; N, 4.88; $C_{18}H_{15}NO_2$ requires; C, 77.96; H, 5.45; N, 5.05%).

b. 6,7-Dimethyl-2-hydroxy-1,4-naphthoquinone

A solution of 2-anilino-6,7-dimethyl-1,4-naphthoquinone (3.1; 0.014 mole) in concentrated sulphuric acid (70ml) was diluted with an equal volume of water and refluxed for 1 minute. After pouring into cold water the precipitated hydroxy derivative was filtered off and extracted into petrol ether (b.p. 100°–102° C). After treatment of the extract with charcoal the title compound separated as a yellow solid, 1.29g (55%), m.p. 175°–177° C (d). (Found; C, 71.29; H, 5.07; $C_{12}H_{10}O_3$ requires; C, 71.28; H, 4.98%)

c. 6,7-Dimethyl-2-hydroxy-3-nitro-1,4-naphthoquinone

Nitration of 6,7-dimethyl-2-hydroxy-1,4-naphthoquinone (1.0g; 0.0056 mole) in chloroform (100ml) as described in example 1(a) afforded 1.027g (87%) of material of m.p. 166°–169° C (d). Recrystallization from ethanol; hydrochloric acid raised the m.p. to 169°–170° C (d). (Found; C, 58.15; H, 3.76; N, 5.74; $C_{12}H_9NO_5$ requires; C, 58.30; H, 3.67; N, 5.6%)

EXAMPLE 8 a. 7-Ethoxy-1-tetralone

A mixture of 4-(p-ethoxyphenyl) butanoic acid (77g, m.p. 136°–138° C, prepared by the Clemmensen reduction of 3-(p-ethoxybenzoyl) propanoic acid) and 85% polyphosphoric acid (500g) was heated with stirring at 80° C for 30 mins. The resulting solution was cooled and poured onto 2Kg of ice-water and the precipitated tetralone extracted into ether. Tge organic phase was washed with water, saturated sodium bicarbonate solution and water, dried (Mg SO$_4$), and the solvent removed. Distillation of the residue afforded the tetralone bp$_{0.1}$ 164°–168° C., 41.62g (60%) as a white solid. Recrystallization from 40°–60° C petrol gave material of m.p. 34°–36° C. (Found; C, 75.65; H, 7.29; $C_{12}H_{14}O_2$ requires; C, 75.76; H, 7.46%)

b. 6-Ethoxy-3-hydroxy-1,4-nephthoquinone

7-Ethoxy-1-tetralone (37g; 0.195 mole) was added to 1 molar solution of potassium t-butoxide in dry t-butanol (1600ml) previously saturated with oxygen and the mixture stirred under an oxygen atmosphere until 0.39 mole of oxygen (2 equivs) were absorbed (ca. 15–30 mins.). The resulting solution was cooled (exothermic reaction), acidified with concentrated hydrochloric acid and the t-butanol removed in vacuo. The residue was partitioned between water and chloroform and the organic phase separated. Extraction of the hydroxy quinone with sodium bicarbonate followed by re-acidification afforded, after filtration and drying 19.57g (46%) of material of m.p. 185° C (d). Recrystallization from ethanol in the presence of charcoal increased the m.p. to 188° C (d). Found; C, 66.13; H, 4.85; $C_{12}H_{10}O_4$ requires; C, 66.05; H, 4.62%)

c. 6-Ethoxy-3-hydroxy-2-nitro-1,4-naphthoquinone

Nitration of 6-ethoxy-3-hydroxy-1,4-naphthoquinone (2g; 0.092 mole) according to example 1(a) yielded 2.38g (99%) of the 2-nitro derivative. Recrystallization from water; hydrochloric acid gave material of m.p. 158° C(d). (Found; C, 54.89; H, 3.61; N, 5.14; $C_{12}H_9NO_6$ requires; C, 54.75; H, 3.45; N, 5.32%).

EXAMPLE 9

6,7-Dimethoxy-2-hydroxy-3-nitro-1,4-naphthoquinone

A solution of 6,7-dimethoxy-2-hydroxy-1,4-naphthoquinone (2g) in chloroform (200ml) was nitrated with fuming nitric acid at room temperature. Work-up as described in example 1(a) gave 1.88g (79%) of nitro derivative of m.p. 178°–181° C. Recrystallization from water; hydrochloric acid gave m.p. 181°–184° C. (Found; C, 51.72; H, 3.30; N, 5.08; $C_{12}H_9NO_7$ requires; C, 51.62; H, 3.25; N, 5.02%).

EXAMPLE 10 a. 6-Bromo-3-hydroxy-1,4-naphthoquinone

Autoxidation of 7-bromo-1-tetralone (4g; 0.0178 mole) as described in example 8(b) afforded 1.52g (34%) of the title compound of m.p. 197° C. Recrystallization from ethanol raised the m.p. to 216° C. (Found; C, 47.50; H, 2.12; Br, 31.43; $C_{10}H_5BrO_3$ requires; C, 47.49; H, 1.99; Br, 31.60%).

b. 6-Bromo-3-hydroxy-2-nitro-1,4-naphthoquinone

Nitration of 6-bromo-3-hydroxy-1,4-naphthoquinone (0.82g) in chloroform (100ml) as described in example 1(a) gave 0.80g (81%) of the nitro derivative, m.p. 172° C. (Found; C, 40.30; H, 1.43; N, 4.55; Br, 26.80; $C_{10}H_4BrNO_5$ requires; C, 40.29; H, 1.35; N, 4.70; Br, 26.81%).

EXAMPLE 11 a. 7-Fluoro-1-tetralone

A stirred mixture of 4-(p-fluorophenyl) butanoic acid (23g; 0.126 mole) and 85% polyphosphoric acid (200g) was heated at 100° C for 4 hrs., cooled, and poured onto ice-water (800g). After thorough stirring the precipitated tetralone was filtered off, washed well with water, and recrystallized from ethanol to give 13.07g (63%) of material of m.p. 56–57° C. (Found; C, 73.31; H, 5.72; $C_{10}H_9FO$ requires; C, 73.13; H, 5.53%).

b. 6-Fluoro-3-hydroxy-1,4-naphthoquinone

Autoxidation of 7-fluoro-1-tetralone (13g) as described in example 8(b) gave 5.6g (37%) of the naphthoquinone which after recrystallization from chloroform had m.p. 206°–210° C. (Found; C, 62.50; H, 2.70; $C_{10}H_5FO_3$ requires; C, 62.51; H, 2.62%).

c. 6-Fluoro-3-hydroxy-2-nitro-1,4-naphthoquinone

Nitration of 6-fluoro-3-hydroxy-1,4-naphthoquinone (1.0g) as described in example 1(a) afforded 0.81g (66%) of product of m.p. 152° C. (Found; C, 50.28; H, 1.61; H, 5.61; $C_{10}H_4FNO_5$ requires; C, 50.65; H, 1.70; N, 5.91%).

EXAMPLE 12 a. 6,7-Diethyl-1-tetralone 3-(3′,4′-Diethylbenzoyl) propanoic acid (m.p. 93° C, prepared by the acylation of 1,2-diethyl benzene with succinic anhydride) was catalytically reduced to 4-(3′,-4′-diethylphenyl) butanoic acid (b.p.$_{0.7}$ 143°–147° C). A mixture of this acid (59g; 0.27 mole) and 85% polyphosphoric acid (450g) was warmed to 80° C with stirring for 30 mins. and worked up as in example 8(a) to yield 48.30g (89%) of 6,7-diethyl-1-tetralone, b.p.$_{0.7}$ 118°122° C. (Found; C, 82.95; H, 9.21; $C_{14}H_{18}O$ requires; C, 83.12; H, 8.97%). Alternatively 4-(3′,4′-diethylphenyl butanoic acid (23.3g; 0.106 mole) may be cyclized by stirring at 100° C with 80% sulphuric acid (115ml) for 1 ½ hrs. After dilution, extraction into ether and distillation 15.53g (74%) of the tetralone was recovered.

b. 6,7-Diethyl-2-hydroxy-1,4-naphthoquinone

Autoxidation of 6,7-diethyl-1-tetralone (48g; 0.24 mole) with potassium t-butoxide in t-butanol as described in example 8(b) afforded 34.60g (63%) of the title compound. Recrystallization from aqueous ethanol in the presence of charcoal gave a yellow crystalline solid of m.p. 105°–109° C. (Found; C, 70.45; H, 6.10; $C_{14}H_{14}O_3·½H_2O$ requires; C, 70.28; H, 6.32%).

c. 6,7-Diethyl-2-hydroxy-3-nitro-1,4-naphthoquinone

Nitration of 6,7-diethyl-2-hydroxy-1,4-naphthoquinone (2.0g) as described in example 1(a) gave 1.794g (75%) of material of m.p. (EtOH; $H_2O$; HCl) 152° C (d). (Found; C, 60.74; H, 4.94; N, 4.87; $C_{14}H_{13}NO_5$ requires C, 61.09; H, 4.76; N, 5.09%).

EXAMPLE 13 a. 6,7-Tetramethylene-1-tetralone 4-(3′4′-Tetramethylenphenyl) butanoic acid (33g; 0.14 mole) was cyclized with 85% polyphosphoric acid as described in example 8(a) to yield 24.04g (85%) of tetralone b.p.$_{0.3}$ 146°–148° C. The product solidified in the receiver and was recrystallized from light petrol [bp 40–60°] to give m.p. 48° C. (Found; C, 84.15; H, 8.21; $C_{14}H_{16}O$ requires; C, 83.96; H, 8.05%).

b. 2-Hydroxy-6,7-tetramethylene-1,4-naphthoquinone

Autoxidation of 6,7-tetramethylene-1-tetralone (15.0 g 0.0694 mole) according to the procedure of example 8(b) gave after recrystallization from aqueous ethanol, 2.96g (17%) of material of m.p. 193° C. (Found; C, 73.44; H, 5.34; $C_{14}H_{12}O_3$ requires; C, 73.67; H, 5.30%).

c. 2-Hydroxy-3-nitro-6,7-tetramethylene-1,4-naphthoquinone

Nitration of 2-hydroxy-6,7-tetramethylene-1,4-naphthoquinone (1g) in chloroform as described in example 1(a) gave 0.97g (81%) of yellow nitro derivative of m.p. 149° C (d). Recrystallization from aqueous ethanol; hydrochloric acid raised the m.p. to 195°–196° C (d). (Found; C, 61.52; H, 4.10; N, 4.87; $C_{14}H_{11}NO_5$ requires; C, 61.54; H, 4.06; N, 5.13%).

EXAMPLE 14 a. 7-Phenyl-1-tetralone 4-(4′-Biphenylyl) butanoic acid (80g, 0.333 mole m.p. 116° C prepared by the Clemmensen reduction of 3-(4′-biphenylcarbonyl) propanoic acid) was cyclized with 85% polyphosphoric acid as described in example 8(a) to give 20.98g (30%) of the tetralone m.p. 67° C after recrystallisation from 40–60 petrol. (Found; C, 86.30; H, 6.53, $C_{16}H_{14}O$ requires; C, 86.45; H, 6.35%).

b. 2-Hydroxy-7-phenyl-1,4-naphthoquinone

Autoxidation of 7-phenyl-1-tetralone (19g; 0.085 mole) according to the procedure of example 8(b) gave after recrystallization from ethanol in the presence of charcoal 9.47g (44%) of yellow product of m.p. 190°–192° C. A further recrystallization gave m.p. 192° C. (Found; C, 86.68; H, 4.03; $C_{16}H_{10}O_3$ requires; C, 76.69; H, 4.03%).

c. 2-Hydroxy-3-nitro-7-phenyl-1,4-naphthoquinone

Nitration of 2-hydroxy-7-phenyl-1,4-naphthoquinone (2.0g) as described in example 1(a) afforded 2.14g (91%) of 3-nitro derivative of m.p. 164° C (d). Recrystallization from ethanol; hydrochloric acid gave m.p. 172°–173° C. (Found; C, 64.73; H, 3,34; N, 4.78; $C_{16}H_9NO_4$ requires; C, 65.09; H, 3.05; N, 4.79%).

| Biological Results: | Dose (mg/Kg) | Time (mins) | % Inhibition of PCA response |
|---|---|---|---|
| Example 1 | | | |

-continued

| Biological Results: | Dose (mg/Kg) | Time (mins) | % Inhibition of PCA response |
|---|---|---|---|
| 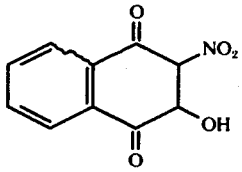 | 25<br>100<br>25<br>100 | 0<br>0<br>30<br>30 | 31<br>32<br>16<br>30 |
| Example 2<br>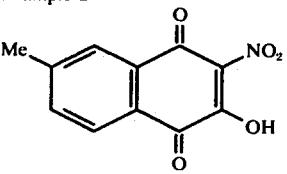 | 25<br>100<br>25<br>100 | 0<br>0<br>30<br>30 | 15<br>56<br>33<br>30 |
| Example 3<br>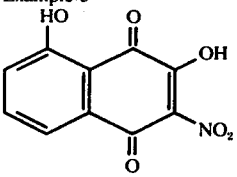 | 25<br>72<br>25<br>72 | 0<br>0<br>30<br>30 | 24<br>44<br>14<br>18 |
| Example 4<br>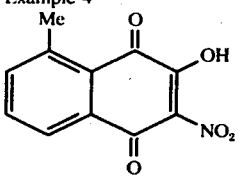 | 0.5<br>1.0<br>2.0<br>4.0 | 10<br>10<br>10<br>10 | 6<br>16<br>16<br>29 |
| Example 5<br>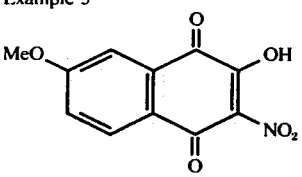 | 5<br>10<br>20<br>40 | 10<br>10<br>10<br>10 | 22<br>41<br>65<br>85 |
| Example 6<br>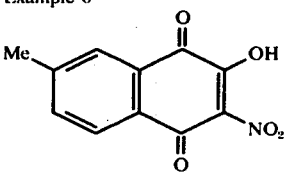 | 5<br>10<br>20<br>40 | 10<br>10<br>10<br>10 | 19<br>36<br>33<br>52 |
| Example 7<br>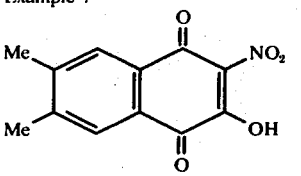 | 25<br>100<br>25<br>100 | 0<br>0<br>30<br>30 | 62<br>90<br>18<br>27 |
| Example 8<br>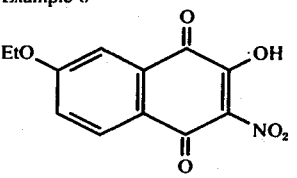 | 5<br>10<br>20<br>40 | 10<br>10<br>10<br>10 | 25<br>28<br>54<br>79 |

Example 9

| Biological Results: | Dose (mg/Kg) | Time (mins) | % Inhibition of PCA response |
|---|---|---|---|
| 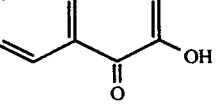 | 5 | 10 | 28 |
| | 10 | 10 | 39 |
| | 20 | 10 | 75 |
| | 40 | 10 | 84 |
| Example 10 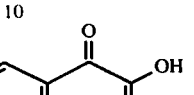 | 100 | 10 | 5 |
| | 100 | 30 | 13 |
| Example 11 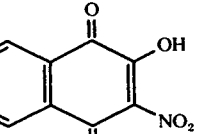 | 100 | 10 | 13 |
| | 100 | 30 | 16 |
| Example 12 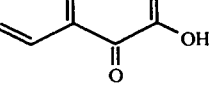 | 1 | 10 | 11 |
| | 2 | 10 | 23 |
| | 4 | 10 | 26 |
| | 8 | 10 | 55 |
| Example 13  | 5 | 10 | 72 |
| | 10 | 10 | 80 |
| | 20 | 10 | 87 |
| | 40 | 10 | 90 |
| Example 14 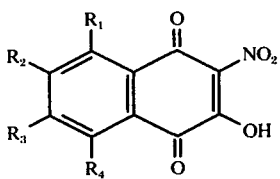 | 10 | 10 | 20 |
| | 20 | 10 | 12 |
| | 40 | 10 | 23 |
| | 80 | 10 | 23 |

We claim:

1. A compound of the formula:

(I)

or a pharmaceutically acceptable salt thereof, wherein $R_1$, $R_2$, $R_3$ and $R_4$ are each hydrogen, lower alkyl, lower alkoxy, phenyl, hydroxy, or halogen, or any adjacent two of $R_1$, $R_2$, $R_3$ and $R_4$ taken together with the carbon atoms to which they are joined form a 5- or 6-membered carbocyclic ring, provided that $R_1$, $R_2$, $R_3$ and $R_4$ are not all hydrogen.

2. A compound according to claim 1 wherein $R_1$ and $R_4$ are each hydrogen, $R_2$ and $R_3$ are each hydrogen or lower alkyl, or $R_2$ and $R_3$ taken together with the carbon atoms to which they are joined form a cyclopentenyl or cyclohexenyl ring, provided that $R_1$, $R_2$, $R_3$ and $R_4$ are not all hydrogen.

3. A compound according to claim 1 wherein $R_1$, $R_2$, $R_3$ and $R_4$ are each hydrogen, fluorine, chlorine, bromine, iodine, alkyl of 1 to 3 carbon atoms, alkoxy of 1 to 4 carbon atoms or phenyl, or $R_1$ and $R_2$, or $R_2$ and $R_3$, or $R_3$ and $R_4$ taken together with the carbon atoms to which they are joined form a benzene, cyclohexenyl or cyclopentenyl ring, provided that $R_1$, $R_2$, $R_3$ and $R_4$ are not all hydrogen.

4. A compound according to claim 1 wherein one of $R_1$, $R_2$, $R_3$ and $R_4$ is methyl, ethyl, methoxy, ethoxy, hydroxy or fluorine and the rest are each hydrogen; two of $R_1$, $R_2$, $R_3$ and $R_4$ are methyl, ethyl or methoxy and the rest are each hydrogen; one of $R_1$, $R_2$, $R_3$ and $R_4$ is phenyl and the rest are each hydrogen; or $R_2$ and $R_3$ are tetramethylene and $R_1$ and $R_4$ are each hydrogen.

5. An alkaline metal, an alkaline earth metal, an amino or an amine salt of a compound of claim 1.

6. The sodium, potassium, magnesium or aluminum salt of a compound of claim 1.

7. The compound according to claim 1 which is 2-hydroxy-6,7-dimethyl-3-nitro-1,4-naphthoquinone.

8. The compound according to claim 1 which is 2-hydroxy-6,7-diethyl-3-nitro-1,4-naphthoquinone.

9. The compound according to claim 1 which is 2-hydroxy-6,7-trimethylene-3-nitro-1,4-naphthoquinone.

10. The compound according to claim 1 which is 2-hydroxy-6,7-tetramethylene-3-nitro-1,4-naphthoquinone.

11. A compound according to claim 14 which is in the form of its sodium or potassium salt.

* * * * *